US00PP19457P2

(12) United States Plant Patent
Kordes

(10) Patent No.: US PP19,457 P2
(45) Date of Patent: Nov. 18, 2008

(54) SHRUB ROSE PLANT NAMED 'KORFLOCI04'

(50) Latin Name: *Rosa hybrida*
Varietal Denomination: KORfloci04

(75) Inventor: Tim-Hermann Kordes, Klein Offenseth-Sparrieshoop (DE)

(73) Assignee: W. Kordes' Söhne Rosenschulen GmbH & Co kG, Offenseth-Sparrieshoop (DE)

( * ) Notice: Subject to any disclaimer, the term of this patent is extended or adjusted under 35 U.S.C. 154(b) by 0 days.

(21) Appl. No.: 12/008,681

(22) Filed: Jan. 11, 2008

(51) Int. Cl.
*A01H 5/00* (2006.01)

(52) U.S. Cl. ..... Plt./107

(58) Field of Classification Search ..... Plt./107, Plt./102

See application file for complete search history.

*Primary Examiner*—Annette H Para

(57) ABSTRACT

A new and distinct variety of rose with long lasting, novel blush pink colored flowers, and attractive foliage with good disease resistance. It exhibits compact growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORfloci04'.

BACKGROUND OF THE INVENTION

The new variety of rose plant of the present invention originated from a controlled crossing in a breeding program of two distinct parents during the summer of 1999. The crossing was between 'KORparesni' and 'KORvanaber', both created by the same breeder, Tim-Hermann Kordes.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORfloci04'.

SUMMARY OF THE INVENTION

The new rose plant may be distinguished from its seed parent, 'KORparesni' by the following combination of characteristics:

1. The flowers of 'KORfloci04' are blush pink, while the flowers of the seed parent are pink,
2. The growth habit of 'KORfloci04' is compact, while the growth habit of the seed parent is upright, and
3. 'KORfloci04' exhibits more petals than the seed parent.

The new rose plant may be distinguished from its pollen parent, 'KORvanaber' by the following combination of characteristics:

1. The growth habit of 'KORfloci04' is compact, while the growth habit of the pollen parent is upright, and
2. 'KORfloci04' exhibits more petals than the pollen parent.

The objective of the hybridization was to create a new and distinct rose plant with unique qualities, such as:

1. Compact and uniform growth and flowering;
2. Abundant attractive, recurrent flowers;
3. Attractive and abundant foliage; and
3. Resistance to diseases encountered in landscapes and gardens.

This combination of qualities is not present in prior rose cultivars. These objectives have been substantially achieved and in that distinguish 'KORfloci04' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORfloci04' was selected in May, 2000 from the seedling beds to be asexually propagated for further evaluation. The first asexual propagation of 'KORfloci04' was done by budding to seedling understocks in July, 2000 at the inventor's nursery in Offenseth-Sparrieshoop, Germany.

This initial and other subsequent propagations conducted in controlled environments demonstrate that 'Korfloci04' reproduces true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'KORfloci04'. Specifically illustrated is: a flower bud, partially opened bloom, open bloom, floral parts, sepals, juvenile foliage, stem exhibiting thorns, and leaves.

DETAILED BOTANICAL DESCRIPTION

The following is a description of 'KORfloci04', as observed growing in September, 2007 in a nursery in Jackson County, Oreg. on plants of 3 years of age. Color references are made using the Royal Horticultural Society (London, England) Colour Chart, 2001 except where common terms of color are used.

For a comparison, several physical characteristics of the rose variety 'KORgretaum', a rose variety from the same inventor described and illustrated in U.S. Plant Pat. No. 16937 and issued on Aug. 1, 2006 are compared to 'KORfloci04' in Chart 1.

CHART 1

| Characteristic | 'KORfloci04' | 'KORgretaum' |
|---|---|---|
| Flower bud color ¼ open (upper surface) | Red Group 56C | White Group 157D with intonations of Greyed-Red Group 179A |
| Open flower diameter | 70-75 mm | 50-65 mm |
| Incidence of thorns per 10 cm of stem | 20-25 | 8-10 |

Parents:

*Seed parent.*—'KORparesni'.

*Pollen parent.*—'KORvanaber'.

Classification:

*Botanical classification.*—*Rosa hybrida*, 'KORfloci04'.

*Commercial classification.*—Shrub.

FLOWER AND FLOWER BUD

Blooming habit: Recurrent.

Flower bud:

*Size.*—Upon opening, 20–25 mm in length from base of receptacle to end of bud and 18–22 mm diameter at its widest point.

*Bud form.*—Short. Ovoid to globular.

*Bud color.*—As sepals first unfold, but color is Yellow-White Group 158D. When ¼ open, the upper surface of the petals is Red Group 56C, and the lower surface is White Group N155B. Guard petals with intonations of Yellow-Green Group 150C on outer surface and Red Group 47B and Red Group 47C on margins of exposed petals.

*Sepals.*—Size: Average 20–22 mm long×6–8 mm wide. Shape: Sepals generally subulate. Sepal apex is generally cirrose. Strong foliaceous appendages on three of the five sepals. Base is flat at union with receptacle. Quantity: Five. Margins: With stipitate glands. Surface texture: Inner surface: Covered in fine white-grey hairs. Outer surface: Smooth. Stipitate glands are present. Color: Upper surface Yellow-Green Group 146B. Lower surface Yellow-Green Group 144A.

*Receptacle.*—Surface: Smooth. Color: Yellow-Green Group 144A. Shape: Funnel. Size: 5–6 mm (h)×4–6 mm (w).

*Peduncle.*—Surface: Smooth. Length: 40 mm average length. Diameter: 1.0–1.5 mm average diameter. Color: Yellow-Green Group 144B. Strength: Strong. Borne: Multiple flower buds per stem, generally 2 to 5.

Flower bloom:

*Fragrance.*—Moderate.

*Duration.*—On the plant 5 to 6 days. Senesced petals drop away cleanly.

*Size.*—Large sized blooms. When open, the average flower diameter is 70–75 mm and the average flower height is 34 mm.

*Form.*—Shape of flower when viewed from the side: Upon opening, upper part: Flat. Upon opening, lower part: Flat. Open flower, upper part: Flat. Open flower, lower part: Concave.

Color:

*Upon opening, petals.*—Outermost petals: Outer Side: White Group N155B. Inner Side: Red Group 56D. Innermost petals: Outer Side: Red Group 56D. Inner Side: Red Group 56B.

*Upon opening, basal petal spots.*—Basal petal spot, outermost petals: Outer Side: Green-Yellow Group 1D. Inner Side: Green-Yellow Group 1D. Basal petal spot, innermost petals: Outer Side: Green-White Group 157D. Inner Side: Green-White Group 157D.

*After opening, petals.*—Outermost petals: Outer Side: White Group N155C. Inner Side: Red Group 156C. Innermost petals: Outer Side: White Group N155C. Inner Side: Red Group 56B.

*After opening, basal petal spots.*—Basal petal spot, outermost petals: Outer Side: Green-White Group 157D. Inner Side: Green-Yellow Group 1D. Basal petal spot, innermost petals: Outer Side: Green-White Group 157D. Inner Side: Green-Yellow Group 1D. Variegations: Occasional intonations on the outer surface of the guard petals. Color: Yellow-Green Group 150C with Red Group 47B and Red Group 47C.

General tonality: On open flower Red Group 56B. No change in the general tonality at the end of the $6^{th}$ day. Afterwards, general tonality is White Group N155D.

Petals:

*Petal count.*—Approximately 65 petals under normal conditions.

*Petal reflex.*—Petals reflex somewhat.

*Petal edge.*—Ruffled.

*Petal shape.*—Deltoid. Apex shape is round. Shape of base is acute.

*Petal size.*—35–45 mm long; 30–40 mm wide.

*Thickness.*—Average.

*Petal arrangement.*—Generally in a regular pattern with overlapping edges.

Petaloids: Present.

*Petaloid count.*—Average of 6–10 per flower.

*Petaloid edge.*—Smooth. Color of inner margin Green-Yellow Group 1C.

*Petaloid shape.*—With point in center of margin. Shape is linear to elliptic.

*Petaloid texture.*—Smooth.

*Petaloid size.*—Petaloids are 16–18 mm long and 7–9 mm wide.

*Petaloid color.*—Color of inner side is Red Group 49A. Color of outer side is Red Group 56C.

Reproductive organs:

*Pistils.*—Approximately 30–35 present. Stigmas: Location: Superior in position to anthers. Color: Yellow Group 2B. Styles: Length: 7–8 mm long. Color: Yellow-Green Group 154D. Intonations of Greyed-Purple 186B on upper portion of styles.

*Stamens.*—Approximately 30 on average and regularly arranged. Anthers: Size: 3–4 mm long. Color: Yellow-Orange Group 20B. Pollen: Absent. Filaments: Color: Yellow-Green Group 154B. Length: 3–4 mm.

THE PLANT

*Plant growth.*—Moderate vigor. Compact habit. When grown as a budded nursery plant the average plant height is 70–75 cm and the average plant width is 60–65 cm.

*Stems.*—Stem color: Young wood: Green Group 143C. Older wood: Green Group 138A. Stem surface: Young wood: Smooth. Older wood: Smooth.

*Prickles.*—Present. Incidence: 20–25 per 10 cm of stem. Size: Average length: 8–9 mm. Color: Immature prickles: Greyed-Red Group 179B with intonations of Greyed-Yellow Group 161A. Mature prickles: Greyed-Yellow Group 162C. Sensecing to Greyed-Orange 166A. Shape: Concave. Anthocyanin: Present. Color Greyed-Purple Group 185.

*Leaves and leaflets.*—Normally 5–7 leaflets on normal leaves in middle of the stem. Leaf size: 90–100 mm (l)×70–80 mm (w). Quantity: Abundant. Texture: Upper side of leaflet: Semi-glossy, smooth, and leathery. Under side of leaflet: Matte, rough, and leathery. Color, mature foliage: Upper Leaf Surface: Green Group 139A. Lower Leaf Surface: Green Group 138B. Color, juvenile foliage: Upper Leaf Surface: Green Group 137A. Lower Leaf Surface: Green Group 138B. Anthocyanin intonation: Present. Location: Intonations present on juvenile leaf margins, upper leaf surface, and lower leaf surface. Color: Greyed-Purple 187A and Greyed-Purple Group 187B.

*Stipules.*—Size: 17 mm long. Average 8 mm between the tips of the stipule. Main body of stipule 6 mm in width. Shape: Elongated, winged. Stipule color: Margins: Green Group 137C. Center: Yellow-Green Group 145C. Anthocyanin Greyed-Red Group 182A. Presence of stipitate glands: Present on margins. Margins: Serrated. With stipitate glands.

*Petiole.*—Length: 6 mm. Diameter: 1–2 mm. Petiole color: Margins: Green Group 137C. Center: Yellow-Green Group 145D. Anthocyanin not present. Underneath: A few small prickles underneath. Stipitate glands: Limited numbers of stipitate glands on margins.

*Rachis.*—Length: 10–13 mm. Diameter: 1–1.5 mm. Color: Green Group 137C. Anthocyanin not present. Margins: With stipitate glands. Prickles: A few small prickles underneath. Stipitate glands: Limited numbers of stipitate glands on margins.

*Leaflets.*—Size: Average size of the terminal leaflet is 40–45 mm (l)×25–30 mm (w). Shape: Ovate. Base: Ovate. Apex: Acute. Margins: Serrated. Texture: Thick and leathery.

Hips/Seed formation: None observed.

Winter hardiness: To date, the variety has been grown successfully in Zone 5.

Disease resistance: Very good resistance to powdery mildew, rust, and Black spot disease under normal growing conditions.

I claim:

1. A new and distinct variety of rose plant characterized by the following combination of characteristics:

(a) forms attractive, long lasting blush pink flowers;

(b) exhibits compact growth habit;

(c) propagates well using traditional methods, and;

(d) exhibits very good resistance to disease under normal growing conditions, substantially as herein illustrated and described.

* * * * *

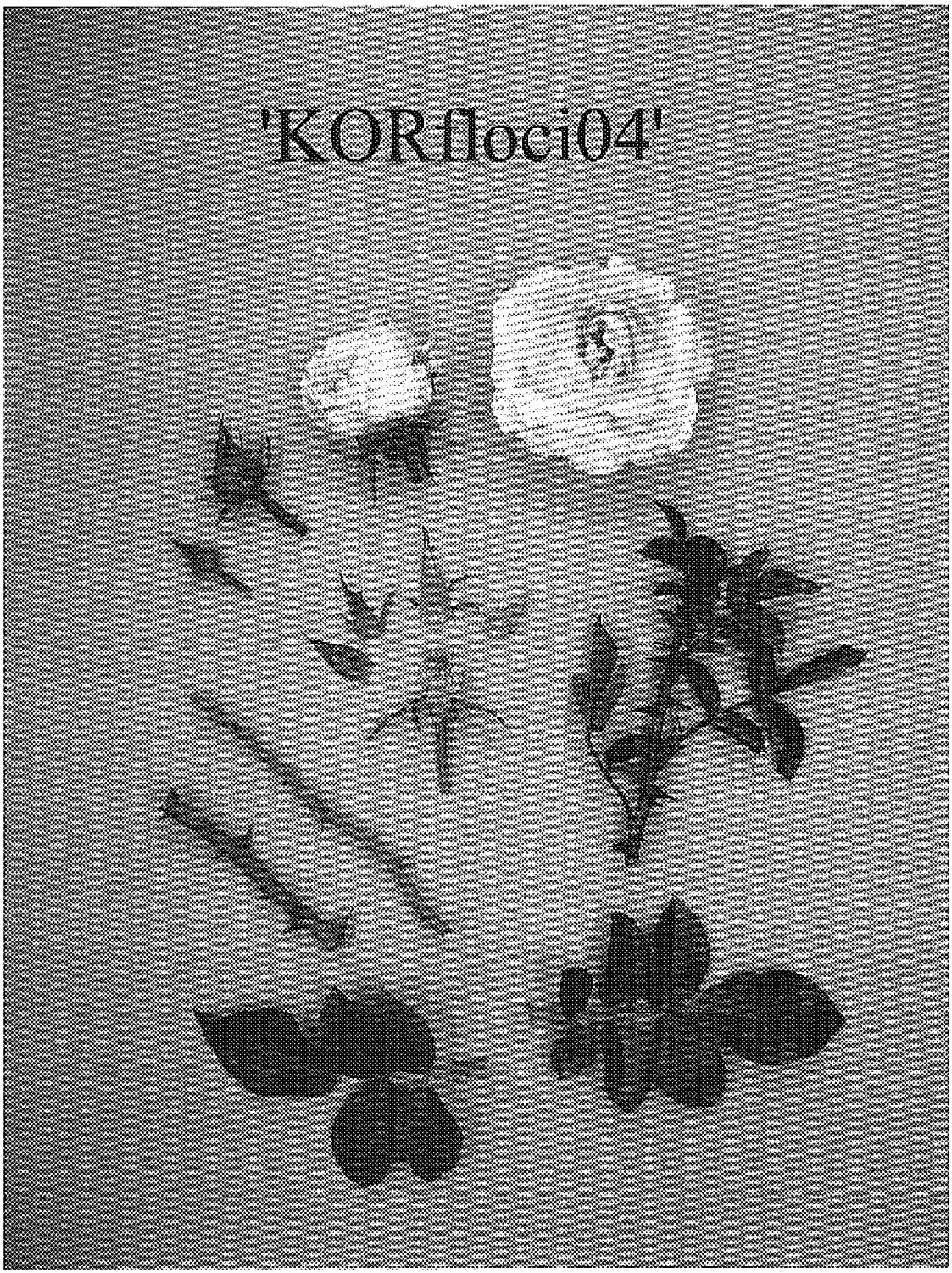
'KORfloci04'